US005590782A

United States Patent [19]

Haber et al.

[11] Patent Number: 5,590,782

[45] Date of Patent: Jan. 7, 1997

[54] VIAL HOLDER ASSEMBLY

[75] Inventors: Terry M. Haber, Lake Forest; William H. Smedley, Lake Elsinore; Clark B. Foster, Laguna Niguel, all of Calif.

[73] Assignee: Habley Medical Technology Corporation, Laguna Hills, Calif.

[21] Appl. No.: 423,425

[22] Filed: Apr. 17, 1995

[51] Int. Cl.$^{6}$ .......... B65D 85/30; A61B 19/02

[52] U.S. Cl. .......... 206/528; 206/535; 206/583; 206/593; 220/663; 215/249

[58] Field of Search .......... 206/591, 592, 206/594, 583, 540, 535, 528; 220/662, 663; 215/247, 249

[56] References Cited

U.S. PATENT DOCUMENTS

| | | | |
|---|---|---|---|
| 4,159,764 | 7/1979 | Schinke | 206/583 |
| 4,366,912 | 1/1983 | Matukura | 215/247 |
| 4,441,621 | 4/1984 | Matukura | 215/247 |
| 4,545,479 | 10/1985 | Figari | 220/662 |
| 4,664,277 | 5/1987 | Connor | 215/249 |
| 5,316,146 | 5/1994 | Graff | 206/591 |

*Primary Examiner*—Paul T. Sewell
*Assistant Examiner*—Luan K. Bui
*Attorney, Agent, or Firm*—Townsend and Townsend and Crew

[57] ABSTRACT

A vial holder assembly (2) includes a generally conventional vial (4) housed within a vial holder (6). Vial holder includes a cup-shaped body (8) and a removable lid (16) mounted to the open end (14) of the body to enclose the vial therein. In one embodiment the lid is designed to coact with or engage with a plastic removable cap (46) mounted to the top of the vial. The removable cap is attached to an annular, frangible central region (42) of the metal closure (38) used to secure the resilient septum (40) to the vial. Removing the cap simultaneously removes the lid and frangible central portion to provide user access to the septum. Another embodiment positions the vial within the body using locating/shock absorbing members (18, 24) situated between the sidewalls (10, 23) and the bottoms (26, 12) of the body and the vial. These accommodate different size vials and help to prevent damage to the vial from physical abuse.

25 Claims, 3 Drawing Sheets

VIAL HOLDER ASSEMBLY

BACKGROUND OF THE INVENTION

Some pharmaceuticals, especially drugs used in chemotherapy, are extremely dangerous to handle. In their concentrated form many of these pharmaceuticals can cause burns on the skin requiring skin grafts to heal if even a drop is inadvertently splashed onto the skin of a health care worker.

These dangerous pharmaceuticals are typically administered after being withdrawn from a vial using a syringe and then injected from the syringe into an I.V. bag for the intravenous administration of the drug in a diluted form. It is during this transfer process that the health care worker is most likely to be exposed to the dangerous pharmaceutical. The necessary handling and manual manipulation of the syringe and vial can result in the vial being dropped and broken, causing this dangerous material to spray or splash unpredictably. In addition to being dangerous, a broken vial can result in the loss of pharmaceutical which is expensive or in limited supply, or both.

SUMMARY OF THE INVENTION

The present invention is directed to a vial holder assembly, including a vial holder and a vial, which helps protect the vial against breakage and facilitates access to the elastomeric septum of the vial.

A vial holder assembly includes a generally conventional vial housed within a vial holder. Vial holder includes a cup-shaped body having a sidewall with a base at one end and an open end at the other. A removable lid is mounted to the open end of the sidewall of the body so to enclose the vial within a region defined by the body and the lid. In one embodiment the lid is designed to coact or engage with a removable plastic cap mounted to the top of the vial. The removable cap is attached to an annular frangible central portion region of a metal closure used to secure the resilient septum to the top of the vial. In this way removing the cap also removes the lid and the annular, frangible central portion of the metal closure at the same time.

In another embodiment the vial is positioned within the body using locating/shock absorbing members situated at least between the sidewalls of the body and vial, and preferably also between the base of the body and bottom of the vial. These locating/shock absorbing members not only permit different size vials to be used with the same vial holder, but also help to prevent damage to the vial in the event the vial holder assembly is dropped or otherwise subjected to rough handling or physical abuse.

The vial is preferably effectively locked within the body of the vial holder. One way of doing so is by using resilient locking flanges extending from the sidewall of the body and engaging the shoulder of the vial.

Another feature of the invention is the incorporation of an inspection lens into the vial holder. The inspection lens is preferably a one-piece element molded from the same material as the base. The inspection lens aids quality control inspection of the contents of the vial by magnifying the contents of the vial.

Other features and advantages of the invention will appear from the following description in which the preferred embodiment is set forth in conjunction with the accompanying drawings.

DESCRIPTION OF THE PREFERRED EMBODIMENT

Figure 1:
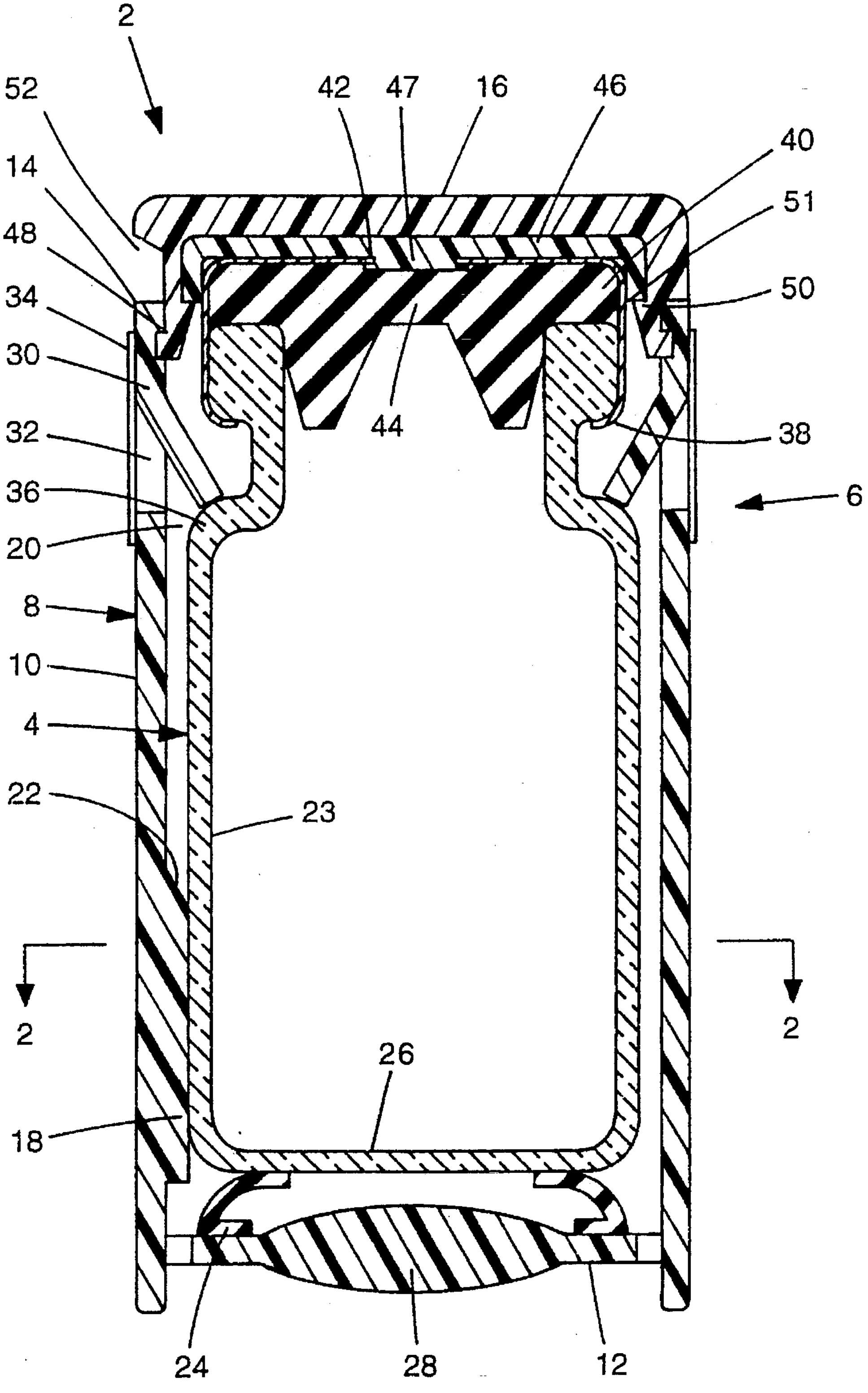
FIG. 1 is a cross-sectional view of an assembled vial holder assembly made according to the invention showing the bottom locating/shock absorbing member in dashed lines when in an unstressed state before the vial is secured in the vial holder.

FIG. 1 illustrates a vial holder assembly 2 including a vial 4 and a vial holder 6. Vial holder 6 including broadly a cup-shaped body 8 having a circumferential sidewall 10 with a base 12 at one end and an open upper end 14 at the other. Vial holder 6 also includes a lid 16 removably securable to open upper end 14. Body 8 is preferably made from a clear impact resistant plastic, such as acrylic or polycarbonate, to permit the user to view the contents of vial 4 as well as help protect vial 4 from damage while housed within vial holder 6. Lid 16 is preferably made of acrylic or polycarbonate and can be translucent, transparent or opaque.

Body 8 includes at least three, and preferably five or six, equally spaced locating/shock absorbing members 18 extending inwardly from sidewall 10. Members 18 are preferably resilient and are one-piece integral members of body 8. As suggested in FIG. 2, members 18 extend generally tangentially and inwardly from sidewall 10 into the interior 20 of vial holder 6. The upper edges 22 of members 18 are angled downwardly (see FIG. 3) so to guide vial 4 towards the center of body 8 and also cause members 18 to deflect radially outwardly towards sidewall 2 and be captured between sidewall 10 of body 8 and sidewall 23 of vial 4. This permits vial holder 6 to securely hold a range of different sizes of vials 4. Body 8 also includes an annular elastomeric bumper 24 positioned on base 12 and configured to engage the bottom 26 of vial 4 so to keep bottom 26 spaced apart a short distance from base 12. Bumper 24 is configured and sized so that in the event vial holder assembly 2 is jarred, such as by being dropped, bumper 24 can absorb some of the impact force. Thus bumber 24 acts as a bottom locating/shock absorbing member.

Body 8 has an inspection lens 28 formed as an integral part of base 12. Inspection lens 28 facilitates quality control of the contents of vial 4 by magnifying the view through the bottom 26 of the vial.

Once inserted into body 8, vial 4 is effectively locked therein by the engagement of resilient locking fingers 30. Locking fingers 30 are formed as integral, one-piece extensions of body 8 during the molding process, thus leaving openings 32 in sidewall 10. To prevent the escape of broken glass or pharmaceutical in the event that vial 4 happens to break within vial holder 6, a clear protective strip 34 is secured about body 8 to cover openings 32. Locking fingers 30 are sized and positioned so that they pivot radially outwardly as vial 4 is inserted into body 8 and then spring back to engage a shoulder 36 of vial 4 when the vial is fully inserted into body 8. This effectively prevents removal of vial 4 from body 8.

Type of commercially available vial 4 used with assembly 2 uses an aluminum closure 38 to secure an elastomeric septum 40 to the open end of the vial. Closure 38 has a hole formed through its center and a series of perforations spaced a short distance from the hole. This creates an annular frangible central portion 42 which overlays a central, needle accessible region 44 of septum 40. The central opening in closure 38 is sealed using a plastic cap 46. Cap 46 has a central portion 47 which is staked to, and thus flows into, the central opening in closure 38. This causes cap 46 to become secured to closure 38 with annular frangible portion 42 surrounding central portion 47.

To provide access to central region 44 of septum 40, cap 46 is removed from the remainder of vial 4. This pulls away frangible central portion 42 thus exposing region 44 of septum 40.

Figure 2B:
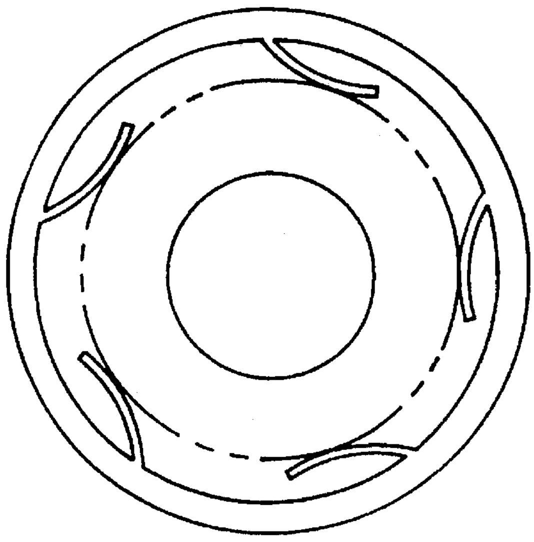
FIGS. 2A and 2B are a cross-sectional views of the body of the vial holder of FIG. 1 taken along line 2—2 of FIG. 1 showing the outside surface of a smaller diameter vial in FIG. 2A and a larger diameter vial in FIG. 2B.
Figure 2A:
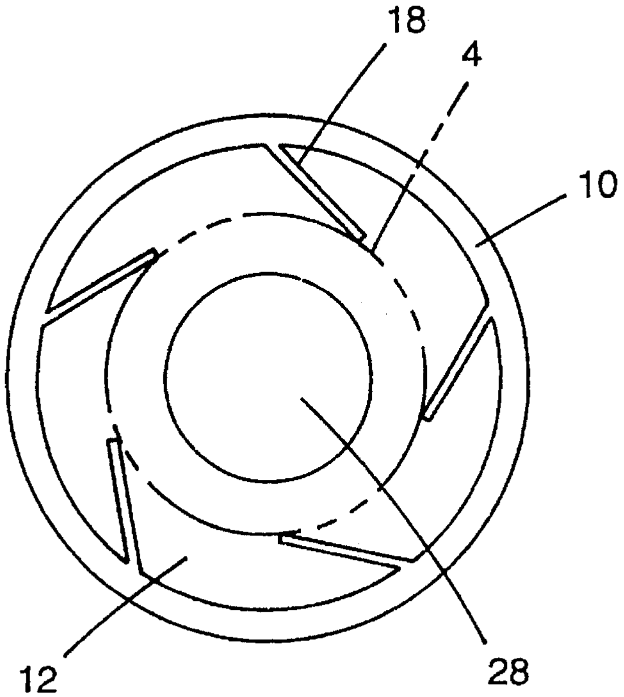
Figure 3:
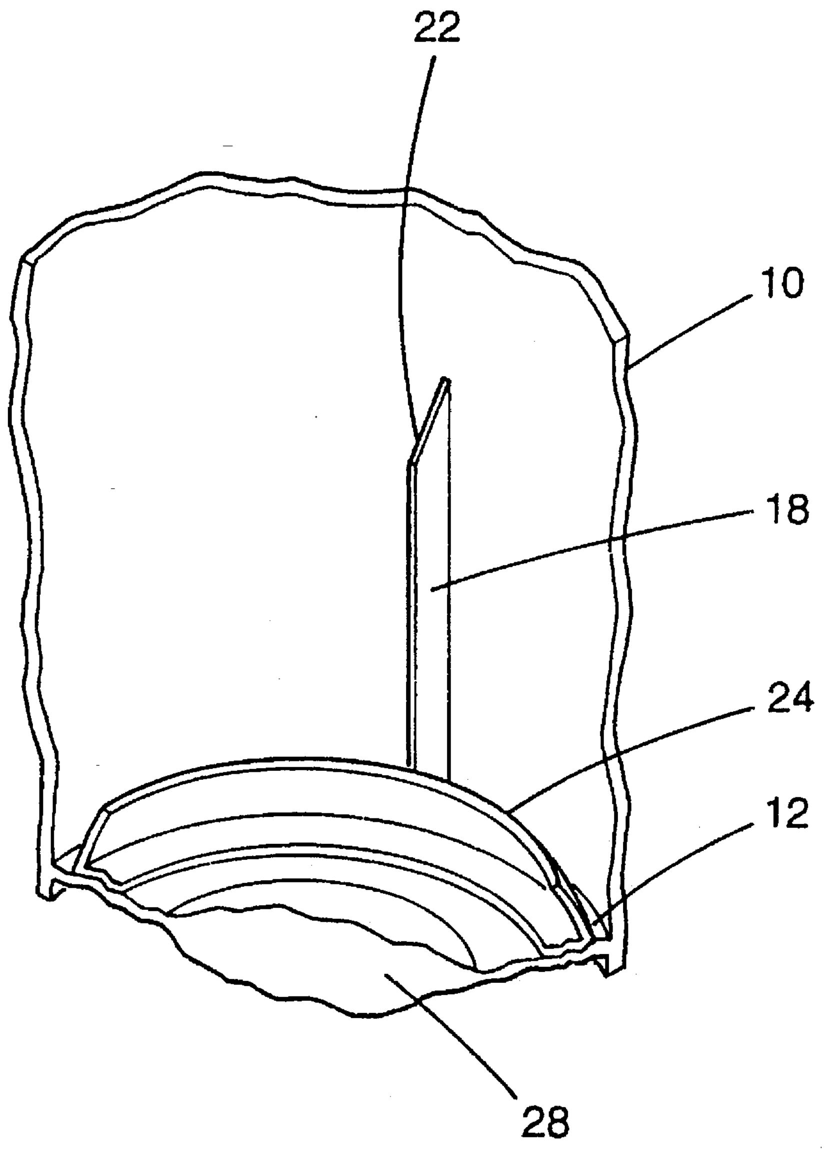
FIG. 3 is a partial sectional view of a portion of the body of FIG. 1 illustrating one side and the bottom of the locating/shock absorbing members.

With the present invention, lid 16 serves a dual function of both enclosing vial 4 within body 8 and engaging cap 46. Lid 16 is secured to open end 14 at a snap-fit region 48. The material from which lid 16 is made is sufficiently flexible so to permit six ramped fingers 50 of lid 16 to deflect sufficiently to permit fingers 50 to engage a lower annular edge 51 of plastic cap 46 as shown in FIG. 2. Lid 16 has a finger access cut-out 52 which permits the user to remove lid 16, and plastic cap 46 therewith, by pushing upwardly on the lid at cut-out 52 and effectively rotating lid 16 about the opposite side of upper end 14. Both the frictional engagement of vial 4 and the use of locking fingers 30, as well as the translational and rotational lifting motion of lid 16, prevents vial 4 from being pulled out of body 8 as lid 16 is removed.

In use, the health care worker places his or her thumb at cut-out 52 and presses upwardly thus causing disengagement of lid 16 from open end 14 at snap-fit region 48 and also lifting plastic cap 46 from closure 38 of vial 4. This causes annular, frangible central portion 42 of closure 38 to be removed and expose central region 44 of septum 40. The contents of vial 4 can now be accessed using a needle cannula passing through central region 44 of septum 40 in a conventional manner. When finished, lid 14, carrying cap 46 therewith, can be remounted to open end 14 for disposal or storage of assembly 2. Depending on the contents of vial 4, inspection of the contents may be facilitated through the use of inspecting lens 28 before or after use.

Modification and variation can be made to the disclosed embodiment without departing from the subject of the invention as defined in the following claims. For example, members 18 are preferably integral one-piece extensions of body 8. However, other types of locating/shock absorbing members could be used between the sidewall 54 of vial 4 and sidewall 10 of body 8 and between bottom 56 and base 12. For example, it may be possible to replace bumper 24 with a resilient, integral member extending from bottom 12. Also, locating/shock absorbing members may be made to absorb energy by being collapsable rather than resilient. Instead of using integrally formed locking fingers 30, vial 4 could be effectively locked within body 8 by using a separate, resilient retaining ring which would be mounted within open end 14 and engage shoulders 36 much as fingers 30 do, but without forming openings 32. Suitable adhesive could also be used to effectively lock vial 4 within vial holder 6. In addition, body 8 could be sized so that open end 14 is positioned somewhat above closure 38 to make it difficult, if not impossible, to remove vial 4 from vial holder 6; the inability to grasp vial 4 coupled with a relatively high frictional resistance to movement could cause vial 4 to be effectively locked within body 8.

What is claimed is:

1. A vial holder assembly comprising:

a vial containing a pharmaceutical, having a top, a vial sidewall and a bottom; and a vial holder comprising:

a body having a body sidewall and a base defining an interior sized to house the vial therein, the body sidewall terminating at an open end;

a locating/shock absorbing member situated between the body sidewall and the vial sidewall;

a removable lid removably mounted to the upper end of the body sidewall so the vial is enclosed within a region defined by the body interior and the lid; and means for effectively preventing the removal of the vial from the body.

2. The assembly according the claim 1 further comprising a base locating/shock absorbing member situated between the base of the body and the bottom of the vial.

3. The assembly according to claim 2 wherein the base locating/shock absorbing member comprises an elastomeric bumper.

4. The assembly according to claim 1 wherein the sidewall locating/shock absorbing member comprises integral extensions of the body sidewall.

5. The assembly according to claim 4 wherein the integral extensions comprise generally tangentially-extending members which resiliently center the vial within the body sidewall.

6. The assembly according to claim 1 wherein the vial removal preventing means includes a locking finger formed integrally with and extending from the body sidewall to create an opening through the sidewall.

7. The assembly according to claim 6 further comprising a sealing strip positioned over said opening.

8. The assembly according to claim 1 wherein said base of said body further comprises a magnifying lens to facilitate inspection of the pharmaceutical within the vial.

9. A vial holder assembly comprising:

a vial containing a pharmaceutical, having a top, a vial sidewall and a bottom;

a vial holder comprising:

a body having a body sidewall and a base defining an interior sized to house the vial therein, the body sidewall terminating at an open end;

a locating/shock absorbing member situated between the body sidewall and the vial sidewall; and a removable lid removably mounted to the upper end of the body sidewall so the vial is enclosed within a region defined by the body interior and the lid;

the vial further comprising an elastomeric septum at least partially covered by a metal closure, said metal closure including a frangible central region, said vial further comprising a removable cap mounted over the metal closure and secured to the central region of the metal closure so that removing the removable cap removes the frangible central region of the metal closure and exposes the elastomeric septum; and said lid comprises a coacting element coacting with the cap of the vial so that removal of the lid also causes removal of the cap and of the frangible central region of the metal closure.

10. The assembly according to claim 9 wherein the removable cap comprises a lower annular edge and the coacting element comprises a resilient catch element engaging the lower annular edge so that lifting upon the lid also lifts up the cap through the engagement of the catch element with the lower annular edge.

11. The assembly according to claim 10 further comprising a plurality of said resilient catch elements.

12. The assembly according to claim 10 wherein said metal closure is made of aluminum.

13. A vial holder assembly comprising:

a vial, containing a pharmaceutical, having a top, a vial sidewall and a bottom, the vial further comprising an elastomeric septum at least partially covered by a metal closure, said metal closure including a frangible central region, said vial further comprising a removable cap mounted over the metal closure and secured to the central region of the metal closure so that removing the removable cap removes the frangible central region of the metal closure and exposes the elastomeric septum; and a vial holder, housing the vial, comprising:

a body including a body sidewall having a base at one end and an open end at another end;

a removable lid mounted to the open end of the body sidewall so to enclose the vial within a region defined by the body and the lid; and said lid comprising a coacting element coacting with the cap of the vial so that removal of the lid also causes removal of the cap and of the frangible central region of the metal closure.

14. The assembly according to claim 13 wherein the removable cap comprises a top surface and a lower annular edge and the coacting element comprises a resilient catch element engaging the lower annular edge so that lifting upon the lid also lifts up the cap through the engagement of the catch element with the lower annular edge.

15. The assembly according to claim 14 further comprising a plurality of said resilient catch elements.

16. The assembly according to claim 13 wherein said metal closure is made of aluminum.

17. The assembly according to claim 13 further comprising:

a sidewall locating/shock absorbing member located between the body sidewall and the vial sidewall.

18. The assembly according to claim 17 further comprising a base locating/shock absorbing member located between the base of the body and the bottom of the vial.

19. The assembly according to claim 18 wherein the base locating/shock absorbing member comprises an elastomeric bumper.

20. The assembly according to claim 17 wherein the sidewall locating/shock absorbing member comprises integral extensions of the body sidewall.

21. The assembly according to claim 20 wherein the integral extensions comprise generally tangentially-extending members which resiliently center the vial within the body sidewall.

22. The assembly according to claim 13 further comprising means for effectively preventing the removal of the vial from the body.

23. The assembly according to claim 22 wherein the vial removal preventing means includes a locking finger formed integrally with and extending from the body sidewall to create an opening through the sidewall.

24. The assembly according to claim 23 further comprising a sealing strip positioned over said opening.

25. The assembly according to claim 13 wherein said base of said body further comprises a magnifying lens to facilitate inspection of the pharmaceutical within the vial.

* * * * *